US00PP36640P2

(12) United States Plant Patent
Horvath

(10) Patent No.: US PP36,640 P2
(45) Date of Patent: Apr. 29, 2025

(54) ***RUDBECKIA* PLANT NAMED 'Green Eyed Lady'**

(50) Latin Name: ***Rudbeckia* hybrid**
Varietal Denomination: Green Eyed Lady

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 56 days.

(21) Appl. No.: 18/445,716

(22) Filed: Dec. 26, 2023

(51) Int. Cl.
*A01H 5/12* (2018.01)
*A01H 6/14* (2018.01)

(52) U.S. Cl.
USPC ..... Plt./474

(58) Field of Classification Search
USPC ..... Plt./474
See application file for complete search history.

*Primary Examiner* — Karen M Redden
*Assistant Examiner* — Zachariah Allan Kay

(57) ABSTRACT

A new and distinct variety of *Rudbeckia* plant as illustrated and described, characterized by the combination of thin foliage, and yellow flowers with green cones compared to the seed parent.

1 Drawing Sheet

Figure 1:
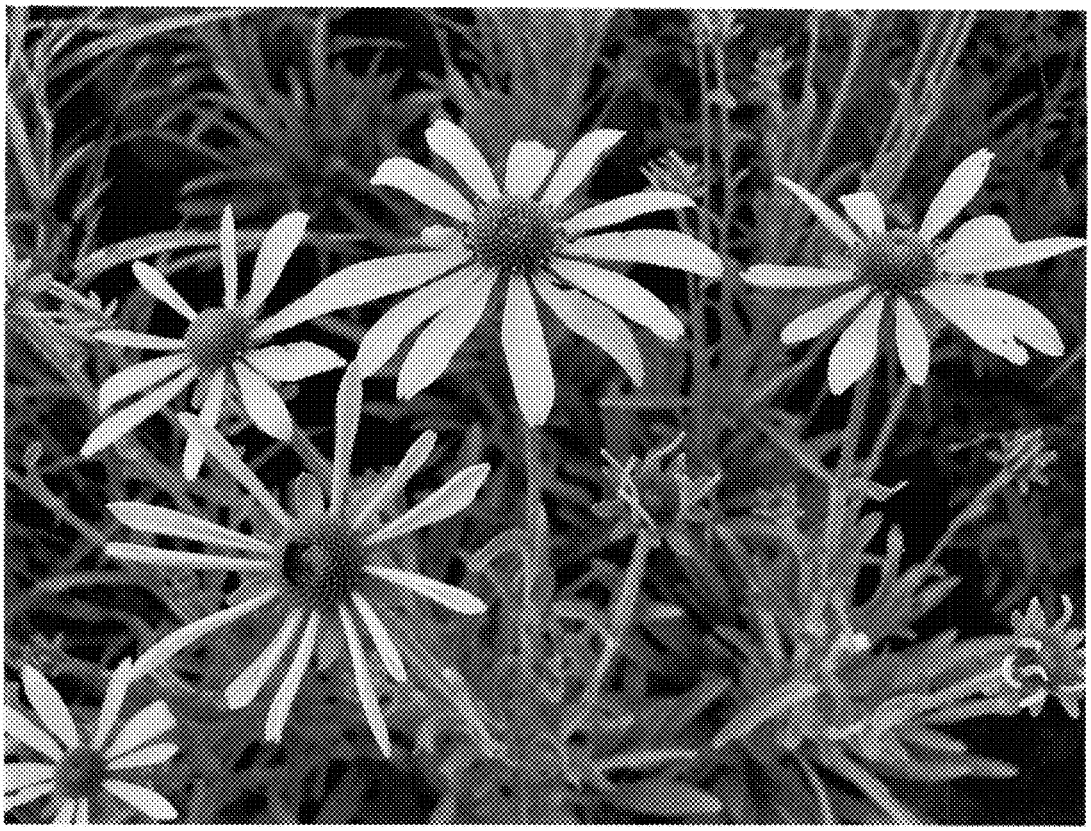

Latin name: *Rudbeckia* hybrid.
Cultivar name: 'Green Eyed Lady'.

BACKGROUND OF THE INVENTION

The present invention relates to a new and distinct hybrid of *Rudbeckia* plant named 'Green Eyed Lady' characterized by the combination of thin hairy foliage and yellow flowers with green cones compared to the seed parent. The new *Rudbeckia* was raised as a seedling from open pollinated seed sown from the seed parent, an unnamed plant of *Rudbeckia missouriensis*, not patented, in Hebron, IL in 2017. The selection of the new plant was due to its' thin hairy foliage, and yellow flowers with green cones compared to the seed parent. Initial asexual reproduction has taken place at a nursery in Hebron, IL since 2018 by means of division, and stem cuttings. The new *Rudbeckia* has shown to be stable and identical in reproduction to the originally discovered plant after rooting over 1000 plants from 2018 to 2023. No plants of the new *Rudbeckia* have been sold in this country, or anywhere in the world, prior to the filing of this application, nor has any disclosure of the new plant been made prior to the filing of this application with the exception of that which was disclosed by the inventor and his nursery, Intrinsic Introductions, Hebron, IL US within one year of filing of this application and was derived directly from the inventor. With the first actual sale taking place on Apr. 4, 2023.

SUMMARY OF THE INVENTION

The new *Rudbeckia* plant named 'Green Eyed Lady' characterized by the combination of thin hairy foliage, and yellow flowers with green cones, have been observed to be unique and stable. For purpose of comparison the new plant will be referred to as 'Green Eyed Lady'.

'Green Eyed Lady' can be compared to plants of *Rudbeckia missouriensis* the seed parent, unnamed, not patented. 1. The new *Rudbeckia* plant has a mature size measuring 60 cm high and 35 cm wide while *Rudbeckia missouriensis* measures 75 cm high and over 60 cm wide. 2.

The new *Rudbeckia* plant has an upright habit while *Rudbeckia missouriensis* has an open habit. 3. The new *Rudbeckia* plant has smaller foliage approximately 20 cm long and 10 mm wide while *Rudbeckia missouriensis* has foliage. that reaches approximately 30-35 cm long and 5 cm wide.

'Green Eyed Lady' can also be compared to the *Rudbeckia* 'American Gold Rush' patented, U.S. Plant Pat. No. 28,498. 1. The new plant has smaller and thinner foliage, 20 cm in length and 10 mm wide while *Rudbeckia* 'American Gold Rush' has foliage 25 cm long and 5 cm wide. 2. The new plant has a yellow flower color RHS 14 A while *Rudbeckia* 'American Gold Rush' plant has a gold flower color RHS 17 A.

'Green Eyed Lady' can also be compared to the *Rudbeckia fulgida* 'Little Gold Star' patented, U.S. Plant Pat. No. 22,397. The new plant has longer and thinner foliage, 20 cm in length and 10 mm wide while *Rudbeckia fulgida* 'Little Gold Star' has foliage 9 cm long and 3.8 cm wide. The new plant has a yellow flower color RHS 14 A while *Rudbeckia fulgida* 'Little Gold Star' plant has a gold flower color RHS 17 A-C.

DESCRIPTION OF PHOTOGRAPHS

Figure 2:
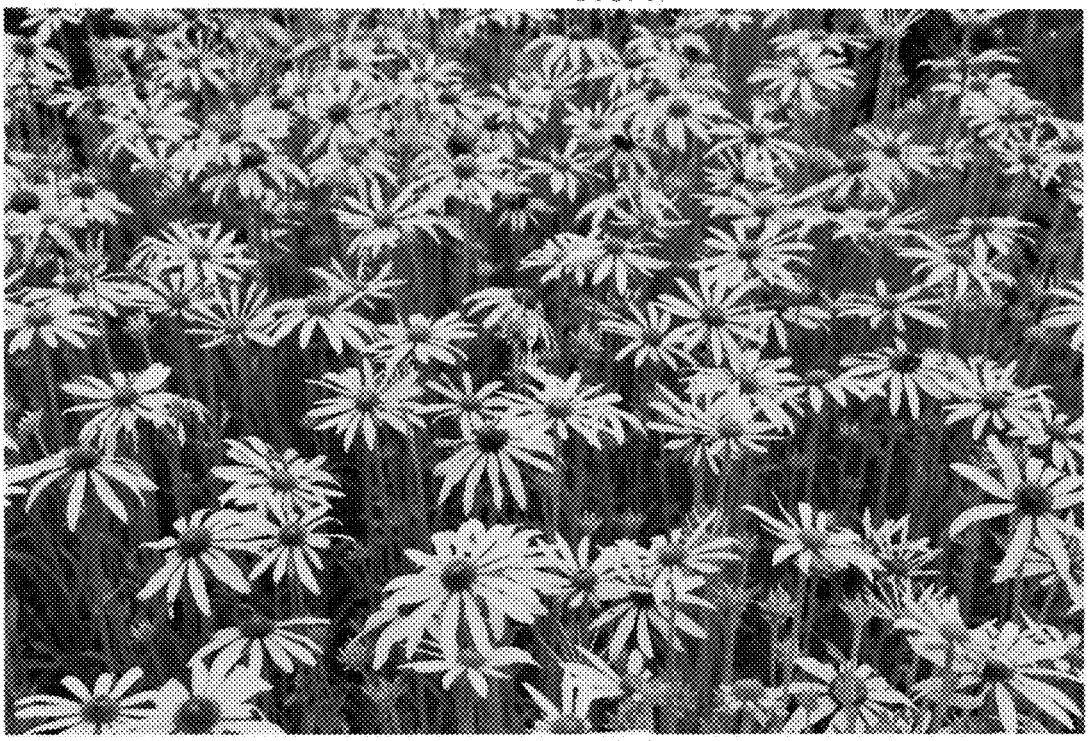

FIG. 1. A close up of the flowers showing foliage below.
FIG. 2. A group of blooming 2 year old plants in July.

DETAILED BOTANICAL DESCRIPTION

In the following description, color references are made to The Royal Horticultural Society Colour Chart 2001 edition. Plants used for the description were grown for two seasons at a nursery in Hebron, IL. Measurements and numerical values represent averages of typical plants.

Botanical classification: *Rudbeckia* cultivar 'Green Eyed Lady'.

*Parentage*.—Male or pollen parent an unknown *Rudbeckia*, female or seed parent an unnamed plant of *Rudbeckia missouriensis*.

*Propagation*.—Vegetative division and stem cutting propagation.

*Root description*.—Fibrous, medium thickness, brown in color.

*Root habit*.—Moderate branching, moderate density.

Plant description: Herbaceous perennial. Overall habit of the new *Rudbeckia* is an upright clump of basal foliage, with branching stems topped by yellow inflorescences starting in July.

*Plant height*.—60 cm. Plant width — 35 cm.

*Primary stem diameter*.—4 mm.

*Primary and secondary stem description*.—branching, with 15 or more leaves. Leaves get smaller as they go up the stem. Strength — strong.

*Primary and lateral stem texture*.—Pubescent with hairs up to 1-2 mm long.

*Secondary stem description*.—Average 17 lateral stems per primary stem.

*Secondary stem length*.—13-15 cm.

*Secondary stem diameter*.—2 mm. Secondary stem internodes — 3 cm.

*Stem color*.—Both 145 B.

Foliage:

*Type*.—Herbaceous.

*Leaf arrangement*.—Alternate, simple, sessile.

*Basal foliage length*.—20 cm Width — 10 mm.

*Stem foliage length*.—9-10 cm Width — 8 mm.

*Shape*.—Lanceolate.

*Apex*.—Acute.

*Base*.—Cuneate.

*Margin*.—Entire.

*Texture*.—Pubescent, soft.

*Venation*.—Pinnate. Venation Color — 145 B.

*Adaxial leaf description*.—Color is 146 B including developing, fully expanded.

*Abaxial leaf description*.—Color is 146 C including developing, fully expanded.

Bud:

*Bud shape*.—Oblate.

*Bud length*.—4 mm. Bud diameter — 8 mm.

*Bud color*.—Close to 144 C.

Inflorescence:

*Inflorescence type*.—Single, composite on branched flowering stems.

*Position*.—Borne on both terminal and axillary peduncles above the foliage.

*Number of inflorescences per plant*.—Approximately 150.

*Arrangement*.—Disc and ray florets.

*Mature center disc*.—15 mm wide and 5 mm height.

*Number of Disc florets*.—200, number of ray florets 13.

*Immature disc floret color*.—144 B.

*Mature disc floret color*.—Brown but close to 200 A.

*Disc floret diameter*.—1 mm at apex, 1 mm at base.

*Disc floret shape*.—Rotate.

*Disc floret length*.—4-5 mm. Disc floret width — 1 mm.

*Disc floret apex*.—Acute.

*Disc floret margin*.—Entire.

*Ray floret size*.—26 mm length and 7 mm width.

*Ray floret color upon opening and in full bloom*.—Adaxial 14 A, Abaxial 163 B.

*Ray floret aspect*.—Initially incurved, then upright, then perpendicular to the peduncle.

*Ray floret shape*.—Lanceolate.

*Ray floret apex*.—Emarginate.

*Ray floret base*.—Obtuse.

*Ray floret margin*.—Entire.

*Ray floret count*.—Approximately 13 per inflorescence.

*Ray floret texture*.—Both the upper and lower surfaces are smooth, glabrous.

*Overall inflorescence size*.—7 cm or more across in diameter with ray florets, 15 mm in height. Receptacle height — 4-5 mm, diameter 1 cm across.

*Bloom period and duration*.—Mid July through September. 6-8 weeks on the plant.

*Blooming habit*.—Upright on 60 cm terminal flowering stems.

Phyllaries:

*Number of phyllaries per inflorescence*.—14 average.

*Length*.—1-2 cm. Width — 2-4 mm.

*Shape*.—Lanceolate.

*Apex*.—Mucronate.

*Base*.—Fused.

*Margin*.—Entire.

*Texture*.—Both upper and lower surface scattered pubescence.

*Color*.—Adaxial 146 B and Abaxial 146 C.

Peduncles:

*Length of both terminal and axillary peduncles*.—20 cm. Diameter — 2 mm.

*Angle*.—Erect to about 15-20 degrees from vertical.

*Strength*.—Strong, Texture-pubescent, Color-145 B.

Reproductive organs:

*Androecium*.—Quantity per disc floret, 5.

*Filament length*.—3 mm. Filament color 145 C.

*Anther shape*.—Oblong. Anther length — 1 mm.

*Anther color*.—14 A.

*Pollen amount*.—Slight but present. Pollen color — 11 D.

*Gynoecium present on ray and disc florets*.—

*Pistils*.—One, length 3 mm.

*Stigma shape*.—Two parted, Stigma color — 200 A.

*Style length*.—4 mm, Style color — 200 A.

*Seed and fruit*.—Achenes, Length — 5 mm. Color — 200 A.

*Scent*.—No scent noticed.

Disease resistance: Resistance to *Septoria* a disease common to *Rudbeckia* has been observed on plants grown under nursery conditions.

Insect resistance: Resistance to insects common to *Rudbeckia* has not been observed on plants grown under nursery conditions to date.

Hardiness: Plants of the new *Rudbeckia* have been observed to be hardy to USDA Zone 5.

I claim:

1. A new and distinct variety of *Rudbeckia* plant named 'Green Eyed Lady' herein as illustrated and described, characterized by the combination thin foliage and yellow flowers with green cones compared to the seed parent.

* * * * *